(12) United States Patent
Chakroun

(10) Patent No.: US 8,777,014 B2
(45) Date of Patent: Jul. 15, 2014

(54) CONTRACEPTION KIT

(76) Inventor: Mohammed Ridha Chakroun, Cagnes sur Mer (FR)

(*) Notice: Subject to any disclaimer, the term of this patent is extended or adjusted under 35 U.S.C. 154(b) by 162 days.

(21) Appl. No.: 13/127,189

(22) PCT Filed: Oct. 16, 2009

(86) PCT No.: PCT/FR2009/001216
§ 371 (c)(1),
(2), (4) Date: May 2, 2011

(87) PCT Pub. No.: WO2010/061065
PCT Pub. Date: Jun. 3, 2010

(65) Prior Publication Data
US 2011/0203949 A1    Aug. 25, 2011

(30) Foreign Application Priority Data
Nov. 3, 2008 (FR) .................. 08 06111

(51) Int. Cl.
*B65D 83/04* (2006.01)
(52) U.S. Cl.
USPC ............................ 206/570; 206/528
(58) Field of Classification Search
USPC .......... 206/223, 531, 532, 538, 570, 438, 528
See application file for complete search history.

(56) References Cited

U.S. PATENT DOCUMENTS

| | | | |
|---|---|---|---|
| 3,737,029 A * | 6/1973 | Serrell et al. ............ | 206/461 |
| 4,855,305 A | 8/1989 | Cohen | |
| 4,958,736 A * | 9/1990 | Urheim .................... | 206/531 |
| 6,156,742 A * | 12/2000 | Mackenzie ............... | 514/170 |
| 6,375,956 B1 * | 4/2002 | Hermelin et al. ......... | 424/400 |
| 7,780,009 B2 * | 8/2010 | Casanova ................. | 206/705 |
| 2002/0066691 A1 * | 6/2002 | Varon ...................... | 206/534 |
| 2004/0222123 A1 * | 11/2004 | Niemann .................. | 206/570 |
| 2008/0175906 A1 * | 7/2008 | Ahmed et al. ............ | 424/464 |
| 2009/0170823 A1 * | 7/2009 | Diliberti .................. | 514/171 |
| 2009/0230013 A1 * | 9/2009 | Born et al. .............. | 206/531 |

FOREIGN PATENT DOCUMENTS

WO    97/42959 A1    11/1997

OTHER PUBLICATIONS

The South Carolina Emergency Contraception Initiative "Getting EC: Using Regular Prescription Birth Control Pills as Emergency Birth Control Pills" [Online] 2006, Retrieved from the Internet: URL:http://www.morningafterinfo.org/gettingec/regular.php [retrieved on Jul. 24, 2013].*
International Search Report of PCT/FR2009/001216, date of mailing Apr. 7, 2010.
Damian McDonald., "Contraceptive Teching Kit" Powerhouse Museum, [Online] 1995, Retrieved from the Internet: URL:http://www.powerhousemuseum.com/collection/database/?irn=378339>[retrieved on 2010-03-08], cited in ISR.

* cited by examiner

*Primary Examiner* — Steven A. Reynolds
(74) *Attorney, Agent, or Firm* — Westerman, Hattori, Daniels & Adrian, LLP

(57) ABSTRACT

The invention relates to a contraception kit that includes at least one regular contraception for the female cycle as well as an emergency contraception. The invention is characterized in that both types of contraception are included in a common packaging.

20 Claims, 2 Drawing Sheets

CONTRACEPTION KIT

FIELD OF THE INVENTION

The present invention relates to a contraceptive kit.

BACKGROUND OF THE INVENTION

Today the use of regular contraception is widespread in the female population and provides efficient contraception. However, this effectiveness is periodically jeopardized because the contraceptives are sometimes forgotten, thus possibly leading to undesired pregnancies. The average rate of omission for women taking the pill is estimated at 30% per female cycle. The specific measures intended to reduce the risk of pregnancy in the case of a forgotten pill reach their limits since for most oral contraceptives the contraceptive effectiveness can generally no longer be ensured when the pill has been taken more than 12 hours late. However, this safety time limit may be reduced to 3 hours for certain contraceptive pills. The undesired pregnancy risk is thus even greater if unprotected sexual intercourse has occurred during the 72 hours preceding the omission. The occurrence of an undesired pregnancy leads, in ¾ of cases, to a voluntary termination of pregnancy. Despite existing emergency contraception, which reduces the risk of pregnancy if it is taken within the 3 to 5 days following unprotected intercourse, the number of legal abortions has generally remained stable and has even increased for women in the youngest age group. Studies have shown that the effectiveness of emergency contraception is time-dependent. It thus appears that in women's everyday life, easy access to emergency contraception is a major criterion for the improvement of its practical effectiveness. Indeed, emergency contraception should ideally be taken as soon as possible after unprotected intercourse or when the pill has been taken with a delay of more than 12 hours. At present, in certain countries such as France, emergency contraception, depending on its composition, may be obtained through medical prescription or sold in pharmacies without prescription, thus reducing the time required to gain access to emergency contraception. However, to obtain an emergency contraceptive, it is necessary to go to a pharmacy. The time between the risky intercourse and access to emergency contraception thus depends on many factors: the time needed to become aware of the risk and to decide to resort to emergency contraception, the availability of a nearby pharmacy, the opening hours and days of the pharmacy, the available means of transportation. Thus, the availability of non-prescription emergency contraception, even though it constitutes an improvement, is not sufficient. One study (Delotte et al., 2007) has indeed shown that in 37.7% of cases, minors do not succeed in obtaining emergency contraception in pharmacies, even though it has been free and anonymous in France since the 2002-39 government decree. Also, even if women anticipate and purchase an emergency contraceptive before ever needing it, they could loose it between the time when it was purchased and the time when they need to use it, or they could forget to renew it, so that by the time they ever need to use it, the emergency contraceptive may be out of date.

SUMMARY OF THE INVENTION

According to the above, a problem which the invention aims to solve is that of increasing the effectiveness of emergency contraceptive means and, in particular, reducing to the maximum possible extent the time required to gain access to an emergency contraceptive means.

The solution proposed by the present invention to solve this problem consists in providing a contraceptive kit, which comprises, on one hand, a regular contraceptive means for at least one female cycle, and on the other hand, an emergency contraceptive means, characterized in that both types of contraceptive means are present in a common packaging.

The kit according to the present invention allows the above-mentioned drawbacks to be overcome. In particular, it comprises a regular contraceptive means and an emergency contraceptive means, wherein both types of contraceptive means are present within a common packaging. Thus, at any given time, the users of a regular contraceptive means may immediately have access to an emergency contraceptive means. This allows the time required to obtain and take an emergency contraceptive, whenever it is needed, to be effectively reduced to zero. This solution thus offers women who have forgotten to take their regular contraception within safe time limits the best possibilities for avoiding undesired pregnancies. Another advantage is that, with the kit according to the present invention, users may access a non-outdated emergency contraceptive at any given time. Specifically, the kit according to the present invention comprises a regular contraceptive means generally designed for one to three female cycles, so that the kit may be renewed on a regular basis, advantageously, every month or every 2 or 3 months. The emergency contraceptive means is thus automatically renewed with the same frequency, before its use-by date has expired. This solution was unexpected because it was quite unconventional to combine a regular contraceptive means with an emergency contraceptive means within a single packaging. Indeed, this solution is contrary to the commonly accepted idea that using a regular contraceptive means eliminates the need for an emergency contraceptive means.

Advantageously, according to the present invention, —the regular contraceptive means is present in a sufficient quantity to ensure contraception for at least one female cycle; —the regular contraceptive means is oral and comprises contraceptive tablets; —the regular contraceptive means comprises a contraceptive ring or contraceptive patch; —the emergency contraceptive means is oral and comprises one or more emergency contraceptive tablets for emergency contraception taken only once or twice; —both types of contraceptive means are each packaged in a separate, so-called primary, packaging; the primary packaging for the regular contraceptive means and the primary packaging for the emergency contraceptive means are joined together by any appropriate means, for example gluing or interlocking; —the primary packaging for the regular contraceptive means and the primary packaging for the emergency contraceptive means are placed in a common packaging referred to as the secondary packaging; —the secondary packaging comprises a box, and each primary packaging comprises a blister pack.

The present invention will be better understood from the following non-limiting description.

According to the present invention, the regular contraceptive means or a contraceptive means which is designed for regular contraception may include, but is not limited to, a contraceptive patch, a contraceptive ring, or any oral contraception means. An oral contraception means is preferred, in particular in the form of tablets, generally referred to as pills.

Generally, a regular oral contraceptive means, in particular the contraceptive pill, is designed to cover one female cycle, or menstrual cycle lasting 28 days, and sometimes 3 to 6 female cycles or more. The regular oral contraceptive means comprises several contraceptive pills, with one pill to be taken each day during the female cycle. Preferably, one pill should be taken each day for 21, 24, 26 or 28 consecutive days, during each 28-day female cycle. If appropriate, when a contraceptive pill must be taken for 21, 24 or 26 days, it may be complemented by a complementary pill to be taken during the 7, 4 or 2 remaining days, respectively. This complementary pill may comprise a placebo and/or an estrogen compound alone. Thus, a regular oral contraceptive means designed to cover one female cycle lasting 28 days, preferably comprises 21, 24, 26 or 28 contraceptive pills, or up to 6 times as many when it is required to cover up to 6 female cycles. Additionally, a regular oral contraceptive means may also cover one cycle that has been artificially extended to several months. For example, an oral contraceptive may be designed for a duration of 84 consecutive days of oral contraceptive treatment, followed by 7 days of interrupted contraception, with, if appropriate, the possible taking of one complementary pill, as seen above. An oral contraceptive may even be designed for a time period of 365 days per year, in which an oral contraceptive is taken permanently.

The regular oral contraception is said to be of the single-phase type when all the pills to be ingested each day during a female cycle have the same composition. It is said to be of the multi-phase type with m phases when the pills have m different compositions, with each of these m compositions specifically corresponding to one time-period of the female cycle, where m lies in the range from 2 to 5.

The regular oral contraceptive means, in particular the contraceptive pill, may comprise a so-called estrogen/progestin combination or a progestin alone or a modulator of the progesterone receptor, that is, hormones which are similar to the estrogens and/or progesterone produced by the ovaries and which block ovulation.

In the case of an estrogen/progestin combination, this may be a combination of an estrogen compound chosen from ethinylestradiol and 17-beta-estradiol or estradiol valerate, and a progestin compound, preferably chosen from norgestimate, levonorgestrel, desogestrel, gestodene, drospirenone, nomegestrol acetate, norethisterone, chlormadinone acetate, cyproterone acetate, dienogest and norgestrel.

Each pill may be dosed so as to deliver a daily dose of 40 micrograms of ethinylestradiol or less, or a dose of 2 milligrams of 17-beta estradiol or estradiol valerate or less, as well as a dose of 250 micrograms or less of norgestimate, a dose of 200 micrograms or less of levonorgestrel, a dose of 150 micrograms or less of desogestrel, a dose of 100 micrograms or less of gestodene, a dose of 3 milligrams or less of drospirenone, a dose of 5 milligrams or less of nomegestrol acetate, or a dose of 2 milligrams or less of norethisterone, chlormadinone acetate, cyproterone acetate, dienogest or norgestrel.

In the case where progestin is the only active ingredient, the progestin compound may be chosen from levonorgestrel, desogestrel or norethisterone. Each pill may be dosed so as to provide a daily dose of 30 micrograms or less of levonorgestrel, a dose of 75 micrograms or less of desogestrel or a dose of 600 micrograms or less of norethisterone.

The regular contraceptive means may also comprise a patch or a contraceptive ring. The contraceptive patch is applied to the skin, generally during the first three weeks of a female cycle, with a different patch each week, and the last week of the cycle being spent without any patch.

The contraceptive ring is placed deep in the vagina, generally remains in this position for the first three weeks of a female cycle, and is then removed during the last week. The patch or the ring delivers the contraceptive hormones regularly, generally estrogen and a progestin, which block ovulation. Thus, in the case where a patch or a ring is the regular contraceptive means, the kit according to the present invention comprises 3 patches or one ring so as to cover the entire female cycle, or may comprise 2 to 6 times these quantities in order to cover 2 to 6 female cycles, most often 3 to 6 cycles.

The emergency contraceptive means, or the means designed for emergency contraception, or the contragestive means, may comprise one or more tablets, conventionally referred to as pills, to be ingested once only. Preferably, the emergency contraceptive means may include 1 tablet comprising 30 mg of ulipristal acetate, 1 tablet containing 1500 micrograms of levonorgestrel or 2 tablets each containing 750 micrograms of levonorgestrel, to be taken once only. The emergency contraceptive means may also comprise 4 tablets each containing 50 micrograms of ethinylestradiol and 250 micrograms of levonorgestrel, to be taken in 2 doses 12 hours apart.

Alternatively, the emergency contraceptive or contragestive means consists of an intrauterine system, in particular an intrauterine device which is inserted by a physician.

According to the present invention, a regular contraceptive means and an emergency contraceptive means are present within a common packaging or packing. According to a preferred embodiment, both types of contraceptive means are each packaged within a separate, so-called primary, packaging, and are then brought together by another so-called secondary packaging, or packing.

According to another embodiment of the present invention, the primary packaging of a regular contraceptive and the primary packaging of an emergency contraceptive are combined together, by any appropriate means, for example gluing or interlocking, without necessarily being packed within a secondary packaging. Both cases offer the advantage that both types of contraceptive means are accessible together at the same time, in particular, through a single purchase, due to the common packaging, but without being mixed together within said packaging.

Preferably, the primary packaging comprises a blister pack. For example, a blister pack comprises a regular contraceptive means in a sufficient quantity for one female cycle, for example 21, 24, 26 or 28 contraceptive pills, and another blister pack comprises an emergency contraceptive means, for example one or more tablets, in a quantity sufficient for it to be taken only once or twice. The regular contraception may also be composed, for one cycle, of 3 patches, each coated with a protective film, or of a vaginal ring enclosed within a specific packaging.

Preferably, the secondary packaging may be a box, which contains both types of contraceptive means, each within its primary packaging. Preferably, the packaging combines a regular contraceptive means intended for one female cycle and an emergency contraceptive means to be taken only once, but it may also comprise a regular contraceptive means intended for several female cycles and/or one emergency contraceptive means to be taken several times. Preferably, a separate primary packaging is provided for each cycle of regular contraception and a separate primary packaging is provided for each use of the emergency contraceptive.

Preferably, the primary packaging has means for distinguishing both types of contraception, for example distinctive colors or symbols.

Alternatively, a regular contraceptive means and an emergency contraceptive means are associated within a primary packaging and combined by means of a so-called secondary packaging or packing. Said primary packaging or blister pack then comprises two separate areas, one for the regular contraception and the other one for the emergency contraception.

The kit according to the invention may further comprise explanatory notes which promote the proper use of both contraceptive methods. In particular, these notes indicate the circumstances and procedures relevant to the use of emergency contraception, with respect to those relevant to the use of regular contraception, as well as the practical follow-up to be observed after such use.

The present invention promotes, in particular, therapeutic education and exchanges between healthcare professionals and women as regards the full range of possibilities offered by available birth control means, in order to reduce the misuse of contraception according to the actual everyday events in women's lives.

Alternatively, the contraceptive means may also be proposed for the regulation of the menstrual cycle, for the treatment of acne, in the case of a premenstrual syndrome or for premenstrual dysphoric disorders. In such cases, women might be less observant than when contraception is the main objective. The usefulness of emergency contraception might thus appear even more clearly in case of need.

BRIEF DESCRIPTION OF THE DRAWINGS

The invention is illustrated in the appended drawings.

DETAILED DESCRIPTION OF PARTICULAR EMBODIMENTS

Figure 1:
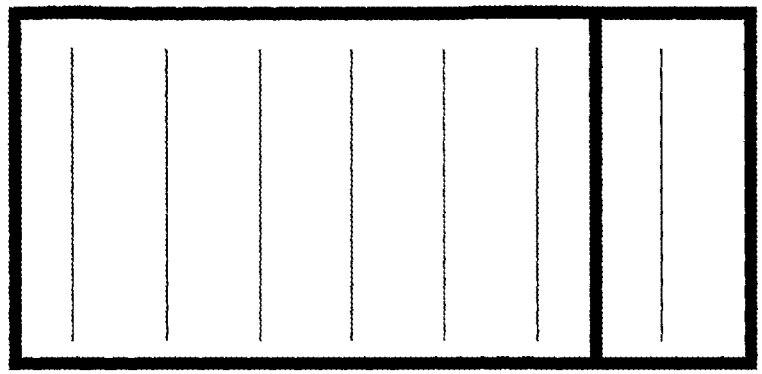
FIG. 1 shows a top view of a box having 2 primary compartments which are joined together side by side.
Figure 2:
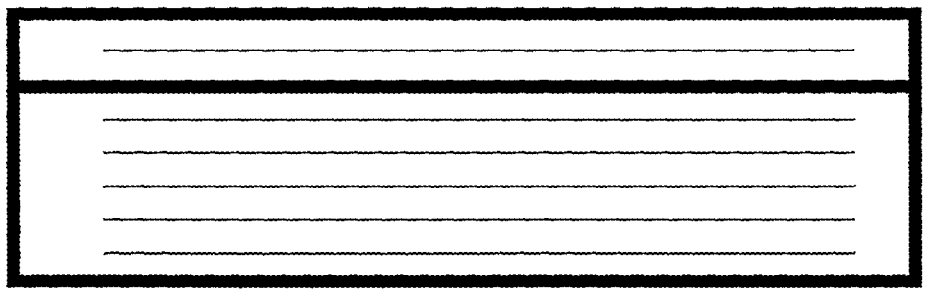
FIG. 2 shows a top view of a box having 2 primary compartments which are joined together back to back.
Figure 3:
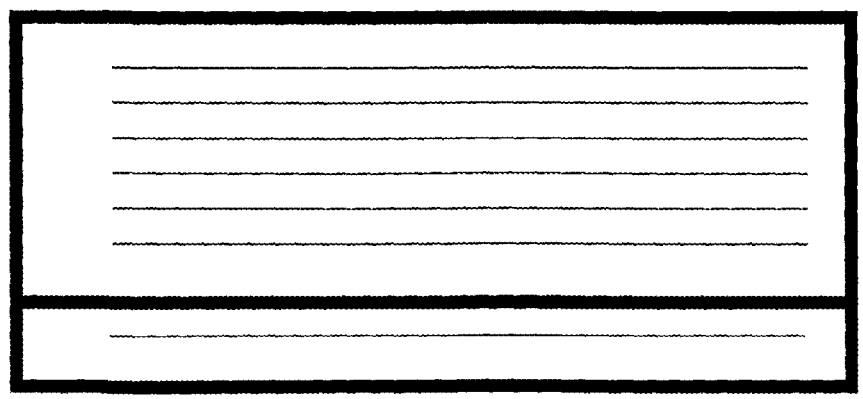
FIG. 3 shows a front view of a double-bottom box.
Figure 4:
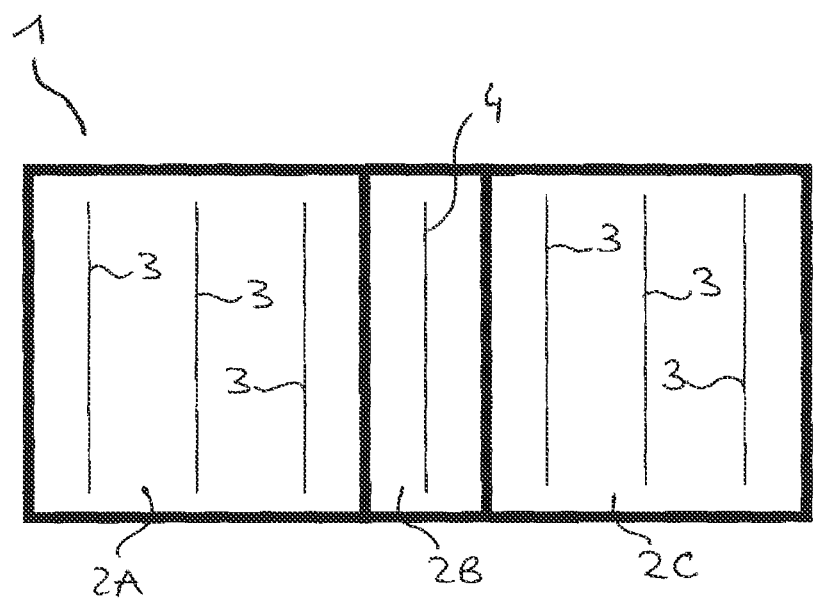
FIG. 4 shows a top view of a 3-compartment box.
Figure 5:
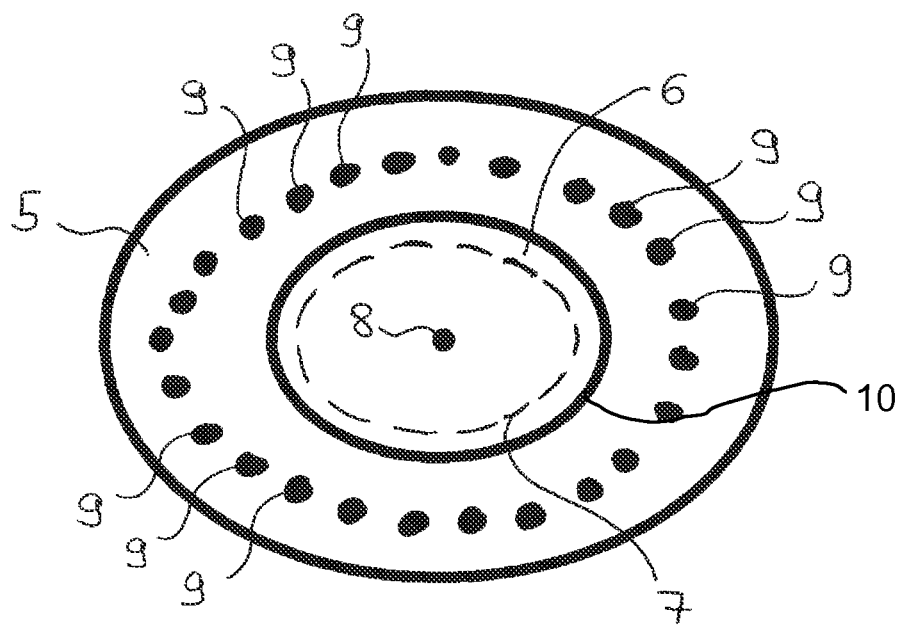
FIG. 5 shows a top view of 2 round or ovoid blister packs interlocked with each other and each comprising one type of contraceptive.

FIGS. 1 to 5 show different embodiments of a kit according to the present invention. In FIG. 1, the secondary packaging is a box 1 having 2 compartments 2A and 2B, placed side by side. Compartment 2A, which is the widest, contains the regular contraceptive, while the other compartment 2B contains the emergency contraceptive. In compartment 2A, the regular contraceptive intended for each cycle is contained within a blister pack 3, while compartment 2A contains one to six blister packs 3, that is, enough for one to six female cycles. In compartment 2B, the emergency contraceptive to be taken only once is contained within a blister pack 4, with compartment 2B preferably containing 1 blister pack 4 to be taken only once, and possibly several blister packs 4 to be taken several times. Box 1 may have one opening (not shown), which opens onto both compartments 2A and 2B, or one opening specific to each of the two compartments 2A and 2B. In FIG. 2, box 1 also comprises 2 compartments 2A and 2B placed back to back, which contain one to six blister packs 3, respectively, each comprising a regular contraceptive for one female cycle, and at least one blister pack 4 comprising an emergency contraceptive. Preferably, both compartments 2A and 2B do not open on the same side, but on the two opposite sides of box 1. In FIG. 3, box 1 also comprises 2 compartments 2A and 2B, each with contents similar to those shown in the preceding figures. Here, compartment 2B is located in a double bottom, that is, box 1 comprises an opening for the largest compartment 2A, whereas an opening for compartment 2B opens at the bottom of compartment 2A (openings not shown). In FIG. 4A, box 1 comprises 3 compartments 2A, 2B and 2C, with the smallest compartment 2B being located between the two others. Compartments 2A and 2C each comprise one to three blister packs 3, each comprising one regular contraceptive for one female cycle, and the center compartment 2B comprises at least one blister pack 4 which contains an emergency contraceptive. Box 1 preferably has three openings, each one for each of the three compartments, which open on the same side or on the two opposite sides of box 1 (openings not shown). Lastly, the embodiment shown in FIG. 5 comprises at least two blister packs, namely a blister pack 5 and a blister pack 6, with rounded or ovoid shapes. Blister pack 5, which has the largest diameter, has a recess 7 in its center, in which the blister pack 6 is placed. The center blister pack 6 contains an emergency contraceptive 8 to be taken at least once, and the outside blister pack 5 contains a regular contraceptive for one female cycle, in the form of pills 9 arranged around its circumference. In the embodiment of FIG. 5, the blister packs are interlocked or glued to each other at 10. This embodiment may comprise several blister packs 5 stacked on top of each other, to cover several cycles of regular contraception. Pills 9 of regular contraceptive may be inserted into a non-return box (not shown), to allow access to one regular pill at a time, for example through a window, each pill becoming available in turn when the box is rotated. Preferably, as regards the emergency contraceptive 8, it is not accessible in the same manner. These different embodiments of a kit according to the present invention allow an emergency contraceptive to be available together with a regular contraceptive and in an easily accessible manner, but in such a way that it is clearly distinguishable from regular contraception.

Of course, the present invention is not limited to the above-described embodiments, and those skilled in the art will readily adapt these embodiments through routine operations.

The invention claimed is:
1. A contraceptive kit comprising:
(i) a regular contraceptive, which covers at least one female cycle, and
(ii) at least one emergency oral contraceptive,
wherein the emergency oral contraceptive is of a different type than the regular contraceptive,
wherein both contraceptives are present in a common packaging and are each packed within a separate primary packaging, and the primary packaging of the regular contraceptive and the primary packaging of the emergency contraceptive are joined together,
wherein the emergency contraceptive is a first pill or a group of first pills, wherein the first pill or each of the first pills contains an emergency amount of a first contraceptive active ingredient or respective emergency amounts of a first combination of contraceptive active ingredients, and
wherein the regular contraceptive is selected from (i) contraceptives other than pills, (ii) pills and groups of pills wherein each of the pills contains (a) a regular contraceptive active ingredient different from the first contraceptive active ingredient or (b) a combination of contraceptive active ingredients different from the first combination, and (iii) pills and groups of pills wherein each of the pills contains (a) the first contraceptive active ingredient in an amount different from the emergency amount or (b) the first combination of contraceptive active ingredients with the amount of at least one of the contraceptive ingredients being different from the respective emergency amount.

2. The contraceptive kit according to claim 1, wherein the regular contraceptive is present in sufficient amount to ensure contraception over at least one female cycle.

3. The contraceptive kit according to claim 1, wherein the regular contraceptive comprises contraceptive tablets.

4. The contraceptive kit according to claim 1, wherein the regular contraceptive comprises a contraceptive ring or contraceptive patch.

5. The contraceptive kit according to claim 1, wherein the emergency contraceptive comprises one or more emergency contraceptive tablets for emergency contraception taken only once or twice.

6. The contraceptive kit according to claim 1, wherein the common packaging comprises a box and each primary packaging comprises a blister pack.

7. The contraceptive kit according to claim 2, wherein the regular contraceptive comprises contraceptive tablets.

8. The contraceptive kit according to claim 2, wherein the regular contraceptive comprises a contraceptive ring or contraceptive patch.

9. The contraceptive kit according to claim 2, wherein the emergency contraceptive comprises one or more emergency contraceptive tablets for emergency contraception taken only once or twice.

10. The contraceptive kit according to claim 3, wherein the emergency contraceptive comprises one or more emergency contraceptive tablets for emergency contraception taken only once or twice.

11. The contraceptive kit according to claim 4, wherein the emergency contraceptive comprises one or more emergency contraceptive tablets for emergency contraception taken only once or twice.

12. The contraceptive kit according to claim 1, wherein the primary packaging of the regular contraceptive and the primary packaging of the emergency contraceptive are joined together by any of gluing and interlocking.

13. The contraceptive kit according to claim 12, wherein the regular contraceptive is oral.

14. The contraceptive kit according to claim 1, wherein the regular contraceptive is oral.

15. The contraceptive kit according to claim 2, wherein the primary packaging of the regular contraceptive and the primary packaging of the emergency contraceptive are joined together by any of gluing and interlocking.

16. The contraceptive kit according to claim 15, wherein the regular contraceptive is oral.

17. The contraceptive kit according to claim 2, wherein the regular contraceptive is oral.

18. The contraceptive kit according to claim 6, wherein the primary packaging of the regular contraceptive and the primary packaging of the emergency contraceptive are joined together by any of gluing and interlocking.

19. The contraceptive kit according to claim 18, wherein the regular contraceptive is oral.

20. The contraceptive kit according to claim 6, wherein the regular contraceptive is oral.

\* \* \* \* \*